US008513240B2

(12) United States Patent
Nagi et al.

(10) Patent No.: US 8,513,240 B2
(45) Date of Patent: *Aug. 20, 2013

(54) MICRONIZED TANAPROGET AND COMPOSITIONS CONTAINING SAME

(75) Inventors: Arwinder S. Nagi, Thiells, NY (US); Ramarao Chatlapalli, Hopewell Junction, NY (US); Shamim Hasan, East Elmhurst, NY (US); Rolland W. Carson, Middletown, NY (US); Mohamed Ghorab, Edison, NJ (US)

(73) Assignee: Wyeth LLC, Madison, NJ (US)

( * ) Notice: Subject to any disclaimer, the term of this patent is extended or adjusted under 35 U.S.C. 154(b) by 203 days.

This patent is subject to a terminal disclaimer.

(21) Appl. No.: 12/975,444

(22) Filed: Dec. 22, 2010

(65) Prior Publication Data

US 2011/0091539 A1 Apr. 21, 2011

Related U.S. Application Data

(63) Continuation of application No. 11/412,022, filed on Apr. 26, 2006, now abandoned.

(60) Provisional application No. 60/675,551, filed on Apr. 28, 2005.

(51) Int. Cl.
*A61K 31/535* (2006.01)

(52) U.S. Cl.
USPC .................................. 514/230.5; 514/170

(58) Field of Classification Search
USPC ....................................................... 514/230.5
See application file for complete search history.

(56) References Cited

U.S. PATENT DOCUMENTS

| | | | |
|---|---|---|---|
| 6,423,699 B1 | 7/2002 | Grubb | |
| 6,436,929 B1 | 8/2002 | Zhang | |
| 6,866,865 B2 | 3/2005 | Hsia | |
| 7,317,037 B2 | 1/2008 | Fensome | |
| 7,496,489 B2 | 2/2009 | Olland | |
| 7,569,564 B2 | 8/2009 | Zhang | |
| 7,569,679 B2 | 8/2009 | Shen | |
| 7,572,779 B2 | 8/2009 | Aloba | |
| 7,582,755 B2 | 9/2009 | Wilk | |
| 7,759,341 B2 | 7/2010 | Tesconi | |
| 7,767,668 B2 | 8/2010 | Nagi | |
| 7,786,297 B2 | 8/2010 | Chatlapalli | |
| 2003/0092711 A1 | 5/2003 | Zhang | |
| 2003/0119796 A1 | 6/2003 | Strony | |
| 2004/0006060 A1 | 1/2004 | Fensome | |
| 2004/0014798 A1 | 1/2004 | Fensome | |
| 2004/0265355 A1 | 12/2004 | Shalaby | |
| 2006/0009428 A1* | 1/2006 | Grubb et al. ................. | 514/170 |
| 2006/0030615 A1 | 2/2006 | Fensome | |
| 2006/0035843 A1 | 2/2006 | Shen | |
| 2006/0142280 A1 | 6/2006 | Zhang | |
| 2006/0246128 A1 | 11/2006 | Nagi | |
| 2006/0247234 A1 | 11/2006 | Nagi | |
| 2006/0280800 A1 | 12/2006 | Nagi | |
| 2010/0189789 A1 | 7/2010 | Nagi | |
| 2010/0267715 A1 | 10/2010 | Tesconi | |

FOREIGN PATENT DOCUMENTS

| | | |
|---|---|---|
| JP | 2002-543192 | 12/2002 |
| JP | 2005-535624 | 11/2005 |
| JP | 2005-535628 | 11/2005 |
| JP | 2007-534760 | 11/2007 |
| JP | 2007-534767 | 11/2007 |
| JP | 2008-505909 | 2/2008 |
| JP | 2008-509216 | 3/2008 |
| JP | 2008-509217 | 3/2008 |
| JP | 2008-509917 | 4/2008 |
| JP | 2008-510722 | 4/2008 |
| JP | 2008-539254 | 11/2008 |
| JP | 2008-539256 | 11/2008 |
| JP | 2008-539258 | 11/2008 |
| JP | 2008-539264 | 11/2008 |
| WO | WO-00/66570 | 11/2000 |
| WO | WO-2004/000230 | 12/2001 |
| WO | WO-2004/000801 | 12/2003 |
| WO | WO-2005/104711 | 11/2005 |
| WO | WO-2005/105817 | 11/2005 |
| WO | WO-2006/014476 | 2/2006 |
| WO | WO-2006/116596 | 11/2006 |

OTHER PUBLICATIONS

Office Action issued in related Chinese Patent Application No. 200680014230.7 dated Jun. 30, 2010.
Office Action issued in related Chinese Patent Application No. 200680014230.7 dated Feb. 24, 2011.
Mitsuru, "Keiko-Toyo-Seizai no Sekkyei to Hyoka", Yakugyo Jiho, Inc., pp. 81-85, Japan (1995).
Japan Pharmaceutical Excipients Council Ed., "Iyakuhin-Tenkabutsu Jiten", Yakuji Nippo Limited, pp. 17, 46, 49, 72, 82, 124, 133, 144, and 214, Japan (Jan. 14, 1994.
English translation of an Office Action issued in related Japanese Patent Application No. 2008-509116 dated Jan. 31, 2012.
Fensome, "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonist Tanaproget" Journal of Medicinal Chemistry, 48:5092-5095 (Jul. 12, 2005).
Zhang, "Novel 6-Aryl-1,4-dihydrobenzo[d][1,3]oxazine-2-thiones as Potent, Selective, and Orally Active Nonsteroidal Progesterone Receptor Agonists", Bioorganic & Medicinal Chemistry Letters, 13:1313-1316 (Apr. 2003).
Winneker, "Nonsteroidal Progesterone Receptor Modulators: Structure Activity Relationships", Seminars in Reproductive Medicine, 23(1):46 (Feb. 2005).

(Continued)

*Primary Examiner* — Jake M. Vu
(74) *Attorney, Agent, or Firm* — Howson & Howson LLP

(57) ABSTRACT

The present invention provides compositions, desirably pharmaceutical compositions, containing micronized tanaproget. The compositions can also contain microcrystalline cellulose, croscarmellose sodium, anhydrous lactose, and magnesium stearate; or can contain microcrystalline cellulose, croscarmellose sodium, sodium lauryl sulfate, povidone, and magnesium stearate. The compositions are useful in contraception and hormone replacement therapy and in the treatment and/or prevention of uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors, and in the preparation of medicaments useful therefor. Additional uses include stimulation of food intake.

16 Claims, No Drawings

(56) References Cited

OTHER PUBLICATIONS

Bapst, "Clinical Pharmacokinetics of Tanaproget, A Non-Steroidal Progesterone Receptor (PR) Agonist, in Healthy Cycling Women During 28 Days of Administration", American Society for Clinical Pharmacology and Therapeutics, Abstract PI-138, (Feb. 2005), p. 44.
Crabtree, "Development of a Mouse Model of Mammary Gland Versus Uterus Tissue Selectivity Using Estrogen- and Progesterone-Regulated Gene Markers", Journal of Steroid Biochemistry & Molecular Biology, 101:11-21 (Sep. 2006; e-published Aug. 22, 2006).
Bapst, "Pharmacokinetics and Safety of Tanaproget, a Nonsteroidal Progesterone Receptor Agonist, in Healthy Women", Contraception, 74:414-418 (Nov. 2006; e-published Sep. 15, 2006).
Bruner-Tran, "Down-Regulation of Endometrial Matrix Metalloproteinase-3 and -7 Expression in Vitro and Therapeutic Regression of Experimental Endometriosis in Vivo by a Novel Nonsteroidal Progesterone Receptor Agonist, Tanaproget", The Journal of Clinical Endocrinology & Metabolism, 91(4):1554-1560 (Apr. 2006; e-published Jan. 17, 2006).
Borka, Crystal Polymorphism of Pharmaceuticals, Acta Pharmaceutica Jugoslavica, Savez Farmaceutiskih Drustava Jugosalavije, Zagreb 40:71-94 (1990).
Rasenack, "Micron-Size Drug Particles: Common and Novel Micronization Techniques", Pharmaceutical Development and Technology, 9(1):1-13 (Jan. 2004).
Remington Pharmaceutical Sciences, 18$^{th}$ Edition, Gennaro et al., Eds., Philadelphia College of Pharmacy and Science, pp. 1319, 1322, and 1323 (1990).
"Sodium Croscarmellose" from http://web.archive.org/web/20031204033945/http://nbent.com/crosscarmellose.htm (Dec. 2003).
Dianzhou, Pharmacy, Edition 4, People's Health Press, p. 141 (Apr. 21, 2001).
Guosheng, Technology of Ultramicronization, Chemical Industry Press, pp. 281-282 (Jun. 30, 2004).
"Annual Update 2003/2004—Treatment of Endocrine Disorders" in Drugs of Future, Prous, Ed., 29(11):86-87 (Nov. 2004).
English translation of Dianzhou, Pharmacy, Edition 4, People's Health Press, p. 141 (Apr. 21, 2001).
English translation of Guosheng, Technology of Ultramicronization, Chemical Industry Press, pp. 281-282 (Jun. 30, 2004).
International Search Report and Written Opinion issued in counterpart International Patent Application No. PCT/US2006/016020 dated Oct. 16, 2006.
International Search Report and Written Opinion issued in related International Patent Application No. PCT/US2006/015837 dated Oct. 16, 2006.
International Search Report and Written Opinion issued in related International Patent Application No. PCT/US2006/015813 dated Oct. 16, 2006.
International Search Report and Written Opinion issued in related International Application No. PCT/US2006/015852 dated Oct. 12, 2006.
International Search Report and Written Opinion issued in related International Application No. PCT/US2006/016025 dated Jun. 12, 2007.
International Search Report and Written Opinion issued in related International Application No. PCT/US2006/022150 dated Jan. 19, 2007.
Office Action issued in related U.S. Appl. No. 11/412,014 dated Sep. 19, 2009.
Applicant's Response to the Office Action issued in related U.S. Appl. No. 11/412,014 dated Sep. 19, 2009.
Office Action issued in related U.S. Appl. No. 11/412,014 dated Apr. 16, 2010.
Applicant's Response to the Office Action issued in related U.S. Appl. No. 11/412,014 dated Apr. 16, 2010.
Office Action issued in related U.S. Appl. No. 11/411,523 dated Oct. 1, 2008.
Applicant's Response to the Office Action issued in related U.S. Appl. No. 11/411,523 dated Oct. 1, 2008.
Office Action issued in related U.S. Appl. No. 11/411,523 dated Mar. 4, 2009.
Applicant's Response to the Office Action issued in related U.S. Appl. No. 11/411,523 dated Mar. 4, 2009.
Office Action issued in related U.S. Appl. No. 11/448,965 dated Jul. 13, 2010.
Applicant's Response to the Office Action issued in related U.S. Appl. No. 11/448,965 dated Jul. 13, 2010.
Office Action issued in related U.S. Appl. No. 11/448,965 dated Jan. 28, 2011.

\* cited by examiner

MICRONIZED TANAPROGET AND COMPOSITIONS CONTAINING SAME

CROSS-REFERENCE TO RELATED APPLICATIONS

This application is a continuation of U.S. patent application Ser. No. 11/412,022, filed Apr. 26, 2006, which claims the benefit under 35 USC 119(e) of U.S. Provisional Patent Application No. 60/675,551, filed Apr. 28, 2005. These priority applications are hereby incorporated by reference.

BACKGROUND OF THE INVENTION

Intracellular receptors (IR) form a class of structurally related gene regulators known as "ligand dependent transcription factors". The steroid receptor family is a subset of the IR family, including the progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the cell membrane via passive diffusion, and binds to the IR to create a receptor/ligand complex. This complex binds to specific gene promoters present in the cell's DNA. Once bound to the DNA, the complex modulates the production of mRNA and protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control compositions, typically in the presence of an ER agonist, alternatively they may be used in conjunction with a PR antagonist. ER agonists are used to treat the symptoms of menopause, but have been associated with a proliferative effect on the uterus which can lead to an increased risk of uterine cancers. Co-administration of a PR agonist reduces/ablates that risk.

Tanaproget, 5-(4,4-dimethyl-2-thioxo-1,4-dihydro-2H-3,1-benzoxazin-6-yl)-1H-pyrrole-2-carbonitrile, is a progesterone receptor modulator and is effective in contraception, hormone replacement therapy, and treating carcinomas and adenocarcinomas, dysfunctional bleeding, uterine leiomyomata, endometriosis, and polycystic ovary syndrome.

What is needed in the art are compositions containing tanaproget for administration to a mammalian subject.

SUMMARY OF THE INVENTION

In one aspect, the present invention provides micronized tanaproget and compositions containing the same.

In a further aspect, the present invention provides a composition containing micronized tanaproget, microcrystalline cellulose, croscarmellose sodium, anhydrous lactose, and magnesium stearate.

In still a further aspect, the present invention provides a composition containing micronized tanaproget, microcrystalline cellulose, croscarmellose sodium, sodium lauryl sulfate, povidone, and magnesium stearate.

In another aspect, the present invention provides a process for preparing compositions containing micronized tanaproget.

In a further aspect, the present invention provides kits having compositions containing micronized tanaproget.

Other aspects and advantages of the present invention are described further in the following detailed description of the preferred embodiments thereof.

DETAILED DESCRIPTION OF THE INVENTION

The present invention provides effective pharmaceutical compositions containing micronized tanaproget. The micronized tanaproget can be readily formulated into an oral dosage unit, and is particularly well suited for a directly compressible unit. The inventors have found that tablets or caplets prepared by direct compression of, or capsules containing, the micronized tanaproget compositions of the invention exhibited rapid and complete drug release, as compared to nonmicronized tanaproget. Thus, the compositions of the invention provide for fast drug release.

Briefly, tanaproget is micronized under nitrogen and conventional micronizing techniques, for example with a Trost or jet mill, applied to non-micronized tanaproget. One method of preparation of non-micronized tanaproget is described in U.S. Pat. No. 6,436,929, and generally in US Patent Application Publication No. 2005/0272702, published Dec. 8, 2005. However, the invention is not limited to the method by which the non-micronized tanaproget is produced.

In another embodiment, non-micronized tanaproget is purified by recrystallization. In one embodiment, the tanaproget is recrystallized from acetone and water. In a further embodiment, the tanaproget is dissolved in acetone, the acetone solution heated, water added to the heated acetone solution, and the acetone/water solution cooled to provide purified tanaproget. This purification specifically includes dissolving crude tanaproget in acetone and heating the solution to about 45 to about 51° C. After circulating the heated solution through a carbon filter for at least about 4 hours, the filtered solution was concentrated using procedures known to those of skill in the art. After adding water to the concentrated solution, in one embodiment at a rate which does not cool the refluxing acetone solution, the acetone/water solution was cooled to about −6 to about 0° C. In one embodiment, the acetone/water solution was cooled at a rate of less than about 0.5° C./minute. After holding the batch at the reduced temperature for at least about 3 hours, the precipitated, purified tanaproget is collected using filtration. The collected solid is washed with a water/acetone mixture, in one embodiment washed twice with a 1:1 water/acetone mixture. The washed purified tanaproget is then dried at less than 35° C. for about 4 hours. Further drying at less than about 50° C. was performed to remove residual acetone/water as measured by spectroscopic methods.

In one embodiment, micronized tanaproget prepared according to the present invention has a particle size of less than about 20 µm, less than about 15 µm, or less than about 10 µm. In a further embodiment, 90% of the particles are less than or equal to about 20 µm and 50% are less than or equal to about 15 µm as determined by the Malvern method, which is readily understood by one of skill in the art.

The micronized tanaproget encompasses tautomeric forms of tanaproget and salts derived from pharmaceutically or physiologically acceptable acids, bases, alkali metals and alkaline earth metals. The present invention also includes derivatives of tanaproget, including, but not limited to, esters, carbamates, sulfates, ethers, oximes, carbonates, and the like.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates.

These salts, as well as the nonmicronized and micronized tanaproget can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

Micronized tanaproget discussed herein also encompasses "metabolites" which are unique products formed by processing tanaproget by the cell or patient. In one embodiment, metabolites are formed in vivo.

In one embodiment, the compositions of the invention are prepared by dry mixing micronized tanaproget, based upon the total weight of the unit dose, with the other components of the composition.

As referred to herein below, the term "wt/wt" refers to the weight of one component based on the total weight of the composition. In one embodiment, this ratio does not include the weight of the capsule, the weight of any filler utilized in the capsule, and seal coating, if so utilized.

A. Composition I of the Invention

The compositions of the present invention are formulated to provide rapid release of tanaproget, while simultaneously being stable under conditions of storage. In one embodiment, Composition I contains micronized tanaproget, or a pharmaceutically acceptable salt thereof, microcrystalline cellulose (MCC), croscarmellose sodium, anhydrous lactose, and magnesium stearate.

In one embodiment, micronized tanaproget is present in Composition I of the invention in an amount from 0.08% wt/wt to 0.4% wt/wt of the composition. This amount may be varied, depending upon the amount of micronized tanaproget to be delivered to a patient. In another embodiment, an overage of tanaproget is utilized, e.g., a 5% overage.

The desired therapeutic regimen can be taken into consideration when formulating Composition I of the invention. For example, micronized tanaproget is present in the formulation at about 0.0875% wt/wt, based upon the total weight of the unit dose. In another example, micronized tanaproget is present in the composition at about 0.35% wt/wt based upon the total weight of the unit dose.

Composition I also contains microcrystalline cellulose at about 56% wt/wt of the composition; croscarmellose sodium at about 6% wt/wt of the composition; magnesium stearate at about 0.25% wt/wt of the composition; and anhydrous lactose at about 37% wt/wt of the composition.

In one embodiment, Composition I of the present invention provides about 0.09% micronized tanaproget, about 56.3% wt/wt of microcrystalline cellulose, about 37.3% wt/wt of anhydrous lactose, about 6% wt/wt of croscarmellose sodium, and about 0.25% wt/wt of magnesium stearate.

In another embodiment, Composition I of the present invention provides about 0.35% micronized tanaproget, about 56.2% wt/wt of microcrystalline cellulose, about 37.1 wt/wt of anhydrous lactose, about 6% wt/wt of croscarmellose sodium, and about 0.25% wt/wt of magnesium stearate.

Without limitation as to the method of preparation of a composition of the invention, an example of a suitable micronized tanaproget composition is provided in Table 1.

TABLE 1

| Component | % wt/wt |
| --- | --- |
| Tanaproget, Micronized | 0.0875 |
| Microcrystalline Cellulose | 56.31 |
| Croscarmellose Sodium | 6 |
| Anhydrous Lactose | 37.35 |
| Magnesium Stearate | 0.25 |

Still a further example of a suitable micronized tanaproget composition is provided in Table 2.

TABLE 2

| Component | % wt/wt |
| --- | --- |
| Tanaproget, Micronized | 0.35 |
| Microcrystalline Cellulose | 56.23 |
| Croscarmellose Sodium | 6 |
| Anhydrous Lactose | 37.17 |
| Magnesium Stearate | 0.25 |

Composition I is typically prepared by combining micronized tanaproget, or a pharmaceutically acceptable salt thereof, microcrystalline cellulose (MCC), croscarmellose sodium, anhydrous lactose, and magnesium stearate and mixing or granulating the mixture. In one embodiment, Composition I is prepared by dry mixing or granulating the components therein using techniques such as roller compaction, slugging, or a combination thereof.

The term "roller compaction" as used herein refers to a process by which two or more solid materials are compacted between two rotating rolls, desirably, counter-rotating rolls, to form solid ribbons. These ribbons are then subject to further steps including milling to form a composition of the invention.

The term "slugging" as using herein refers to a process by which two or more solid materials are compressed on a press, typically using presses that are larger than those presses utilized to prepare large tablets. These tablets are then subject to further steps including milling to form a composition of the invention.

The components can also be in extragranular or intragranular forms, as determined by one of skill in the art and as determined by the requirements of the process. In one embodiment, the croscarmellose sodium is in intragranular form. In another embodiment, the croscarmellose sodium is in extragranular form. In yet another embodiment, the magnesium stearate is in intragranular form.

In addition, a variety of apparatuses can be utilized to perform the process of the invention and includes bags of small, medium, and large sizes, screens of varying sizes, and blenders, among others.

The process can also include compacting or milling Composition I, typically using compactors and mills selected by one of skill in the art. The milling step is typically performed on particles of varying sizes, i.e., large particles, powders, and fine powders to obtain a preferential and more uniform particle size. The milling can include several separating, recycling, and screening steps to obtain the desired particle sizes.

In one embodiment, the compositions of the present invention contain particles of an optimal size to permit dissolution of the composition, and in a further embodiment, the particles are less than or equal to about 125 μm. The sizes of the particles of the composition are typically measured by passing the solid composition through screens of varying sizes. In one embodiment, about 7% of the particles are greater than or equal to about 350 μm. In another embodiment, about 26% of the particles are greater than or equal to about 180 μm. In a further embodiment, about 31% of the particles are greater than or equal to about 150 μm. In still another embodiment, about 36% of the particles are greater than about 125 μm. In yet another embodiment, about 46% of the particles are greater than about 89 μm. In a further embodiment, about 52% of the particles are greater than about 75 μm. In still another embodiment, about 67% of the particles are greater than about 45 μm.

If the particles of the compositions are larger than the optimal size and if the same have not yet been encapsulated in a capsule, the same can be subject to further milling and screening steps, among others, to reduce the particle size.

The process typically includes compressing the composition into a form suitable for oral administration and is typically a tablet or caplet. When compressed into a tablet or caplet, one of skill in the art would readily be able to select a suitable tablet press for use in the present invention. However, one example of such a press includes the Stokes® B2 Tablet Press, among others.

In one embodiment, the tablet prepared according to the present invention is encapsulated in a capsule. In a further embodiment, the capsule is a hydroxypropyl methylcellulose (hypromellose) capsule. The capsule can be optionally sealed with the tablet therein or a filler can be added to the capsule containing tablet. In one embodiment, the filler includes MCC, croscarmellose sodium, and magnesium stearate. In another embodiment, the tablet is placed in the capsule prior to adding the filler.

Optionally, the tablets are film-coated. Suitable film-coatings are known to those of skill in the art. For example, the film-coating can be selected from among suitable polymers such as hydroxypropylmethylcellulose, ethyl cellulose, polyvinyl alcohol, and combinations thereof. Other suitable film-coatings can be readily selected by one of skill in the art. In one embodiment, the tablet is coated with an Opadry® seal coat. Where applied, the weight percent of the film coat is generally in the range of 2% wt/wt to 6% wt/wt of the tablet.

When prepared according to the present invention, the tablets, capsules, or tablets-in-capsules containing Composition I release about 86 to about 99% of tanaproget after about 90 minutes. In a further embodiment, the composition releases about 85% of the tanaproget after about 20 minutes.

B. Composition II of the Invention

In another embodiment, a composition of the present invention contains micronized tanaproget, or a pharmaceutically acceptable salt thereof, microcrystalline cellulose, croscarmellose sodium, sodium lauryl sulfate (SLS), povidone (PVP), and magnesium stearate.

In one embodiment, the micronized tanaproget is present in Composition II of the invention in an amount at about 0.1% wt/wt, or 0.01% wt/wt, of the composition. This amount may be varied, depending upon the amount of micronized tanaproget to be delivered to a patient. The desired therapeutic regimen can be taken into consideration when formulating a composition of the invention. In another embodiment, an overage of tanaproget is utilized, e.g., a 5% overage.

Composition II also contains about 90% wt/wt microcrystalline cellulose; about 6% wt/wt croscarmellose sodium; about 2% wt/wt sodium lauryl sulfate; about 1.5% povidone; and about 0.25% wt/wt magnesium stearate.

In one embodiment, Composition II of the present invention typically contains about 0.10% or about 0.1% micronized tanaproget, about 90% wt/wt microcrystalline cellulose, about 6% wt/wt croscarmellose sodium, about 2% wt/wt sodium lauryl sulfate, about 1.5% povidone, and about 0.25% wt/wt magnesium stearate.

Without limitation as to the method of preparation of Composition II of the invention, an example of a suitable micronized tanaproget composition is provided in Table 3.

TABLE 3

| Component | % wt/wt |
| --- | --- |
| Tanaproget, Micronized | 0.1 |
| Microcrystalline Cellulose | 90.15 |
| Croscarmellose Sodium | 6.00 |
| Sodium Lauryl Sulfate | 2.0 |
| Povidone | 1.5 |
| Magnesium Stearate | 0.25 |

Composition II is prepared by combining micronized tanaproget, microcrystalline cellulose, croscarmellose sodium, povidone, sodium lauryl sulfate, and magnesium stearate; and granulating. In one embodiment, Composition II is prepared by dry mixing the components therein. The components of the composition can also be in extragranular or intragranular forms, as determined by one of skill in the art and as determined by the requirements of the process. A variety of apparatuses can be utilized to perform the process of the invention and includes bags of large, medium, and large sizes, screens of varying sizes, and blenders, among others.

The process can also include compacting or milling Composition II, typically using compactors and mills selected by one of skill in the art. The milling step is typically performed on particles of varying sizes, i.e., large particles, powders, and fine powders to obtain a more uniform particle size. The milling can include several separating, recycling, and screening steps to obtain the desired particle sizes.

If the particles of the compositions are larger than the optimal size and if the same have not yet been encapsulated in a capsule, the same can be subject to further milling and screening steps, among others, to reduce the particle size.

In a further embodiment, the compositions of the present invention can be prepared by diluting the other compositions with excipients. Useful excipients for dilution include those set forth below and can include MCC, croscarmellose sodium, and magnesium stearate.

For example, compositions containing lesser amounts of tanaproget are prepared according to the present invention by diluting compositions containing greater amounts of tanaproget. In one embodiment, a composition containing 0.05 mg of tanaproget is prepared by diluting a composition containing 0.075, 0.1, 0.15, 0.2, or 0.3 mg of tanaproget, or by diluting a composition containing 0.075 or 0.1 mg. In a further embodiment, a composition containing 0.075 mg tanaproget is prepared by diluting a composition containing 0.1, 0.15, 0.2, or 0.3 mg of tanaproget. In another embodiment, a composition containing 0.1 mg of tanaproget is prepared by diluting a composition containing 0.15, 0.2, or 0.3 mg of tanaproget. In yet a further embodiment, a composition containing 0.15 mg tanaproget is prepared by diluting a composition containing 0.2 or 0.3 mg of tanaproget. In still another embodiment, a composition containing 0.2 mg of tanaproget is prepared by diluting a composition containing 0.3 mg of tanaproget. In another embodiment, the compositions of the invention prepared by diluting compositions containing higher amounts of tanaproget are diluted with MCC, croscarmellose sodium, and magnesium stearate.

The process typically includes adding Composition II to a capsule, e.g., a hard shell gelatin capsule. Typically, the capsule is a hydroxypropyl methylcellulose or hypromellose capsule.

However, Composition II can be compressed into a tablet or caplet, which can optionally be encapsulated in a capsule. In one embodiment, the capsule is a hydroxypropyl methylcellulose (hypromellose) capsule. When compressed into a tablet or caplet, one of skill in the art would readily be able to select a suitable tablet press for use in the present invention. However, one example of such a press includes the Stokes® B2 Tablet Press, among others. The capsule can be optionally sealed with the tablet therein or a filler can be added to the capsule containing tablet. In one embodiment, the filler includes MCC, croscarmellose sodium, and magnesium stearate. In another embodiment, the tablet is placed in the capsule prior to adding the filler.

If the composition is compressed into a tablet or caplet, the tablets or caplets can optionally be film-coated. Suitable film-coatings are known to those of skill in the art. For example, the film-coating can be selected from among suitable polymers such as hydroxypropyl methylcellulose, ethyl cellulose, polyvinyl alcohol, and combinations thereof. Other suitable film-coatings can be readily selected by one of skill in the art. In one embodiment, the tablet or caplet is coated with an Opadry® seal coat. Where applied, the weight percent of the film coat is generally in the range of 2% wt/wt to 6% wt/wt of the tablet or caplet.

When prepared according to the present invention, the capsules containing Composition II release about 86 to about 99% of tanaproget after about 90 minutes. In a further embodiment, the capsules release about 85% of the tanaproget after about 20 minutes.

C. Stability of the Compositions of the Invention

The compositions of the present invention, including Compositions I and II, are stable over a period of about 1 month for samples stored at varying temperatures and humidities. The term stable as used herein refers to the compositions of the invention which degrade less than about 4%. Typically, it is the tanaproget that degrades in the composition. Compositions I and II are stable at about 20° C./50% relative humidity to about 45° C./75% relative humidity. In one embodiment, Compositions I and II degrade less than about 4% over a period of greater than 1 month at temperatures at or greater than about 25° C. and a relative humidity at or greater than about 60%. Samples were also stable over a period of about 2 months at temperatures of about 2 to about 8° C., optionally in the absence of light and moisture.

In one embodiment, Compositions I and II of the invention are stored at reduced temperatures, in a further embodiment at temperatures of about 5° C. It is desirable that the compositions be stored in the absence of water, air, and moisture.

D. Additional Components of the Compositions of the Invention

Other suitable components can be added to Compositions I and II of the present invention, provided that the same is not already present, and will be readily apparent to one of skill in the art. Typically, the additional components are inert and do not interfere with the function of the required components of the compositions. The compositions of the present invention can thereby further include other adjuvants, syrups, elixirs, diluents, binders, lubricants, surfactants, granulating agents, disintegrating agents, emollients, metal chelators, pH adjustors, surfactants, fillers, disintegrants, and combinations thereof, among others.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, povidone, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone.

Lubricants can include light anhydrous silicic acid, talc, stearic acid, sodium lauryl sulfate, magnesium stearate and sodium stearyl furamate, among others. In one embodiment, the lubricant is magnesium stearate.

Granulating agents can include, without limitation, silicon dioxide, starch, calcium carbonate, pectin, crospovidone, and polyplasdone, among others.

Disintegrating agents or disintegrants can include starch, carboxymethylcellulose, substituted hydroxypropylcellulose, sodium bicarbonate, calcium phosphate, calcium citrate, sodium starch glycolate, pregelatinized starch or crospovidone, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing tanaproget to about 4 to about 6. In one embodiment, the pH of a solution containing tanaproget is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Additional fillers that can be used in the composition of the present invention include mannitol, calcium phosphate, pregelatinized starch, or sucrose.

E. Methods of Using the Compositions

The invention further provides a method of delivering tanaproget to a patient, where the method includes administering a micronized tanaproget dosing unit according to the invention.

The dosage requirements of tanaproget may vary based on the severity of the symptoms presented and the particular subject being treated. Treatment can be initiated with small dosages less than the optimum dose of tanaproget. Thereafter the dosage is increased until the optimum effect under the circumstances is reached. Precise dosages will be determined by the administering physician based on experience with the individual subject treated. In general, the compositions of this invention are most desirably administered at a concentration that will generally afford effective results without causing any unacceptable harmful or deleterious side effects. For example, an effective amount of micronized tanaproget is generally, e.g., about 0.05 mg to about 1 mg, about 0.05 mg to about 0.3 mg, about 0.05 mg, about 0.075 mg, about 0.1 mg, about 0.15 mg, about 0.2 mg, or about 0.3 mg.

These compositions containing micronized tanaproget are therefore useful in contraception and hormone replacement therapy. The compositions are also useful in contraception and the treatment and/or prevention of uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors, and in the preparation of medicaments useful therefor. Additional uses of the compositions include stimulation of food intake.

The compositions of the invention are formed into a suitable dosing unit for delivery to a patient. Suitable dosing units include oral dosing units, such as directly compressible tablets, capsules, powders, suspensions, microcapsules, dispersible powders, granules, suspensions, syrups, elixirs, and aerosols. In one embodiment, the compositions of the present invention are compressed into a tablet, which is optionally added to a capsule, or the compositions are added directly to a capsule. The compositions of the invention can also be formulated for delivery by other suitable routes. These dosing units are readily prepared using the methods described herein and those known to those of skill in the art.

Solid forms, including tablets, caplets, and capsules containing micronized tanaproget can be formed by dry blending tanaproget with the components described above. In one embodiment, the capsules utilized in the present invention include hydroxypropyl methylcellulose (hypromellose) capsule, or a hard shell gelatin capsule. In another embodiment, the tablets or caplets of the present invention that contain tanaproget are film-coated. Suitable film-coatings are known to those of skill in the art. For example, the film-coating can be selected from among polymers such as hydroxypropylmethylcellulose, ethyl cellulose, polyvinyl alcohol, and combinations thereof.

A pharmaceutically effective amount of tanaproget can vary depending on the components of the composition, mode of delivery, severity of the condition being treated, the patient's age and weight, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. Daily dosages can also be lowered or raised based on the periodic delivery.

It is contemplated that when the compositions of this invention are used for contraception or hormone replacement therapy, they can be administered in conjunction with one or more other progesterone receptor agonists, estrogen receptor agonists, progesterone receptor antagonists, and selective estrogen receptor modulators, among others.

When utilized for treating neoplastic disease, carcinomas, and adenocarcinomas, they can be administered in conjunction with one or more chemotherapeutic agents, which can readily be selected by one of skill in the art.

F. Kits of the Invention

The present invention also provides kits or packages containing micronized tanaproget. Kits of the present invention can include tanaproget and a carrier suitable for administration to a mammalian subject as discussed above. In one embodiment, the tablets or capsules are packaged in blister packs, and in a further embodiment in Ultrx™ 2000 blister packs.

The kits or packages containing the compositions of the present invention are designed for use in the regimens described herein. In one embodiment, these kits are designed for daily oral delivery over 21-day, 28-day, 30-day, or 31-day cycles, among others, or for one oral delivery per day. When the compositions are to be delivered continuously, a package or kit can include the composition in each tablet. When the compositions of the present invention are to be delivered with periodic discontinuation, a package or kit can include placebos on those days when the composition is not delivered.

Additional components may be co-administered with Composition I or II of the invention and include progestational agents, estrogens, and selective estrogen receptor modulators.

In one embodiment, the kits are also organized to indicate a single oral formulation or combination of oral formulations to be taken on each day of the cycle, in a further embodiment including oral tablets to be taken on each of the days specified, and in still a further embodiment one oral tablet will contain each of the combined daily dosages indicated.

In one embodiment, a kit can include a single phase of a daily dosage of Composition I or II of the invention over a 21-day, 28-day, 30-day, or 31-day cycle. Alternatively, a kit can include a single phase of a daily dosage of Composition I or II of the invention over the first 21 days of a 28-day, 30-day, or 31-day cycle. A kit can also include a single phase of a daily dosage of Composition I or II of the invention over the first 28 days of a 30-day or 31-day cycle.

In a further embodiment, a kit can include a single combined phase of a daily dosage of Composition I or II of the invention and a progestational agent over a 21-day, 28-day, 30-day, or 31-day cycle. Alternatively, a kit can include a single combined phase of a daily dosage of Composition I or II of the invention and a progestational agent over the first 21 days of a 28-day, 30-day, or 31-day cycle. A kit can also include a single combined phase of a daily dosage of Composition I or II of the invention and a progestational agent over the first 28 days of a 30-day or 31-day cycle.

In another embodiment, a 28-day kit can include a first phase of from 14 to 28 daily dosage units of Composition I or II of the invention; a second phase of from 1 to 11 daily dosage units of a progestational agent; and optionally, a third phase of an orally and pharmaceutically acceptable placebo for the remaining days of the cycle.

In yet a further embodiment, a 28-day kit can include a first phase of from 14 to 21 daily dosage units of Composition I or II of the invention; a second phase of from 1 to 11 daily dosage units of a progestational agent; and, optionally, a third phase of an orally and pharmaceutically acceptable placebo for the remaining days of the cycle.

In another embodiment, a 28-day kit can include a first phase of from 18 to 21 daily dosage units of Composition I or II of the invention; a second phase of from 1 to 7 daily dose units of a progestational agent; and, optionally, an orally and pharmaceutically acceptable placebo for each of the remaining 0 to 9 days in the 28-day cycle.

In yet a further embodiment, a 28-day kit can include a first phase of 21 daily dosage units of Composition I or II of the invention; a second phase of 3 daily dosage units for days 22 to 24 of a progestational agent; and, optionally, a third phase of 4 daily units of an orally and pharmaceutically acceptable placebo for each of days 25 to 28.

In another embodiment, a 28-day kit can include a first phase of from 14 to 21 daily dosage units of a progestational agent equal in progestational activity to about 35 to about 150 µg levonorgestrel, a second phase of from 1 to 11 daily dosage units of Composition I or II of the invention; and optionally, a third phase of an orally and pharmaceutically acceptable placebo for the remaining days of the cycle in which no antiprogestin, progestin or estrogen is administered.

In a further embodiment, a 28-day kit can include a first phase of from 14 to 21 daily dosage units of a progestational agent equal in progestational activity to about 35 to about 100 µg levonorgestrel; a second phase of from 1 to 11 daily dosage units of Composition I or II of the invention; and optionally, a third phase of an orally and pharmaceutically acceptable placebo for the remaining days of the cycle in which no antiprogestin, progestin or estrogen is administered.

In one embodiment, the daily dosage of tanaproget remains fixed in each particular phase in which it is delivered. In a further embodiment, the daily dose units described are to be delivered in the order described, with the first phase followed in order by the second and third phases. To help facilitate compliance with each regimen, in a further embodiment the kits contain the placebo described for the final days of the cycle.

A number of packages or kits are known in the art for the use in dispensing pharmaceutical agents for oral use. In one embodiment, the package has indicators for each day of the 28-day cycle, and in a further embodiment is a labeled blister package, dial dispenser package, or bottle.

The kit can further contain instructions for administering the tanaproget compositions of the present invention.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Preparation of Micronized Tanaproget

Tanaproget prepared according to US Patent Application Publication No. 2005/0272702, published Dec. 8, 2005 was milled using a U-10 Comil mill and thereby micronized using a MC50 Jetpharma Micronizer with an EZFH-1.4 Feeder. Particle size was tested periodically for a particle size of less than about 15 µm, and desirably less than about 10 µm, being distributed throughout 50% of the sample. The micronized tanaproget was packed in triple poly-bagged fiber drums. A desiccant was inserted between the outermost bags and the atmosphere in the bags replaced with nitrogen gas.

Example 2

Directly Compressible Tablet Compositions Prepared by Employing Micronized Tanaproget The tablet compositions for this example were manufactured using the following protocol and using the components of Table 4.

TABLE 4

| Ingredients | Function |
| --- | --- |
| Micronized Tanaproget | Active |
| Microcrystalline Cellulose (MCC), NF, (Avicel PH101) | Filler, Granulation Aid, Disintegrant |
| Anhydrous Lactose | Filler |
| Croscarmellose Sodium NF (Ac-Di-Sol) | Disintegrant |
| Magnesium Stearate (Vegetable Source), NF | Lubricant |
| Capsule Shell | Inactive |

Anhydrous lactose and MCC were passed through a mesh screen and transferred to a 1 cu. ft. PK blender. The blended anhydrous lactose and MCC were passed through a mesh screen into a suitable poly bag. Micronized tanaproget was transferred to a suitable plastic bag. The tanaproget was pre-blended with a portion of the anhydrous lactose/MCC mixture. The pre-blend containing tanaproget/anhydrous lactose/MCC was transferred to the blender containing the remaining portion of anhydrous lactose and MCC and mixed. An intragranular portion of croscarmellose sodium was passed through a mesh screen and pre-blend with a portion of anhydrous lactose and MCC. The pre-blend containing the intragranular croscarmellose sodium/anhydrous lactose/MCC was added to the blender containing the tanaproget and mixed. An intragranular portion of magnesium stearate was passed through a mesh screen and pre-blend with a portion of anhydrous lactose and MCC. The pre-blend containing the intragranular magnesium stearate/anhydrous lactose/MCC was transferred to the blender containing the tanaproget and mixed to form an intermediate composition.

The intermediate composition was compressed using a roller compactor and then milled using a Fitzmill model D6. The milled material was passed through a mesh screen, the large particles separated, and the large particles milled to a powder. The fine powder produced from the milling was compressed and milled to a powder. All of the milled powder was thereby combined in a blender. An extragranular portion of croscarmellose sodium was passed through a mesh screen and pre-blend with a portion of the combined milled powder. The pre-blend containing the extragranular croscarmellose sodium and milled powder was then mixed with the remaining portion of the combined milled powder. An intragranular portion of magnesium stearate was passed through a screen and premixed with a portion of the pre-blend containing the extragranular croscarmellose sodium and milled powder. The premix containing the extragranular magnesium stearate was added to the blender and mixed with the second portion of the pre-blend containing the extragranular croscarmellose sodium and milled powder to form the final composition.

The final composition was then compressed into a tablet using a Stokes® B2 Tablet Press, adjusting the press as necessary. At equally spaced intervals, tablet samples were obtained and stored in double poly-lined containers, desiccants were placed between the two bags, and the bags were stored at reduced temperatures of 2° C. to 8° C. in the absence of light and moisture. Either the stored tablets or freshly prepared tablets were then encapsulated. See Table 5 for the amounts of the components utilized in the four different tablet strengths.

TABLE 5

| | Tablet Strength (mg) | | | | | | | | | | | |
|---|---|---|---|---|---|---|---|---|---|---|---|---|
| | 0.05 | | 0.075 | | 0.1 | | 0.15 | | 0.2 | | 0.3 | |
| Component | Amount (mg) | % wt/wt | Amount (mg) | % wt/wt | Amount (mg) | % wt/wt | Amount (mg) | % wt/wt | Amount (mg) | % wt/wt | Amount (mg) | % wt/wt |
| Micronized tanaproget | 0.05 | 0.0875 | 0.075 | 0.0875 | 0.105 | 0.0875 | 0.158 | 0.0875 | 0.210 | 0.35 | 0.315 | 0.35 |
| Microcrystalline cellulose | 33.79 | 56.31 | 50.68 | 56.31 | 67.57 | 56.31 | 101.35 | 56.31 | 33.74 | 56.23 | 50.61 | 56.23 |
| Anhydrous Lactose | 22.42 | 37.35 | 33.62 | 37.35 | 44.83 | 37.35 | 67.24 | 37.35 | 22.30 | 37.17 | 33.45 | 37.17 |
| Croscarmellose Sodium | 3.60 | 6.00 | 5.40 | 6.00 | 7.20 | 6.00 | 10.80 | 6.00 | 3.60 | 6.00 | 5.40 | 6.00 |
| Magnesium Stearate | 0.15 | 0.25 | 0.225 | 0.25 | 0.30 | 0.25 | 0.45 | 0.25 | 0.15 | 0.25 | 0.23 | 0.25 |

These compositions include a 5% overage of tanaproget to compensate for manufacturing loss during blending and compacting.

For tablet encapsulation of the 0.075, 0.1, 0.15, 0.2, and 0.3 mg tablets, MCC and croscarmellose sodium were passed through a screen, added to a 1-20 cubic foot blender without an intensifier bar installed, and mixed. Magnesium stearate was passed through a screen and mixed with the blend containing MCC and croscarmellose sodium to form the filler. Using a capsule filler, each size #1 capsule shell was filled by placing one tablet into one capsule shell body and flood filling the capsule with the filler. The filled capsule was then closed.

See Table 6 for the amounts of the components added to the inert filler.

TABLE 6

| | Tablet Strength (mg) | | | | | | | | | |
|---|---|---|---|---|---|---|---|---|---|---|
| | 0.075 | | 0.1 | | 0.15 | | 0.2 | | 0.3 | |
| Ingredients | Amount (mg) | % wt/wt | Amount (mg) | % wt/wt | Amount (mg) | % wt/wt | Amount (mg) | % wt/wt | Amount (mg) | % wt/wt |
| Microcrystalline cellulose | 127.725 | 97.5 | 120.90 | 97.5 | 108.23 | 97.5 | 140.4 | 97.5 | 127.72 | 97.5 |
| Croscarmellose Sodium | 2.62 | 2.0 | 2.48 | 2.0 | 2.22 | 2.0 | 2.88 | 2.0 | 2.62 | 2.0 |
| Magnesium Stearate | 0.655 | 0.5 | 0.62 | 0.5 | 0.55 | 0.5 | 0.72 | 0.5 | 0.655 | 0.5 |
| Capsule | 1 #1 Brown HPMC shell | — | 1 #1 Brown HPMC shell | — | 1 #1 Brown HPMC shell | — | 1 #1 Brown HPMC shell | — | 1 #1 Brown HPMC shell | — |

These compositions include a 5% overage of tanaproget to compensate for manufacturing loss during blending and compacting.

Example 3

Capsule Compositions Prepared by Employing Micronized Tanaproget

The capsule compositions for this example are manufactured using the following protocol and using the components set forth in Table 7.

TABLE 7

| Ingredients | Function |
|---|---|
| Micronized Tanaproget | Active |
| Microcrystalline Cellulose (MCC), NF, (Avicel PH101) | Filler, Granulation Aid, Disintegrant |
| Croscarmellose Sodium NF (Ac-Di-Sol) | Disintegrant |
| Magnesium Stearate, (Vegetable Source), NF | Filler |
| Povidone, K-17, USP | Binder |
| Sodium Lauryl Sulfate (SLS), NF | Surface active agent |
| Capsule Shell | Inactive |

Micronized tanaproget was added to a first plastic bag. A first portion of MCC was combined with the tanaproget and mixed. A second portion of MCC was combined with the blend of tanaproget and MCC and mixed. The blend containing both portions of MCC and tanaproget was passed through a #20 hand screen into a larger bag. The first plastic bag was rinsed with third and fourth portions of MCC, the rinsed products passed through the #20 hand screen into the larger bag, and mixed. A fifth portion of MCC was passed through a #20 hand screen into the larger plastic bag and mixed. A sixth portion of MCC was passed through a #20 hand screen into the larger plastic bag and mixed. A seventh portion of MCC was passed through a #20 hand screen into a suitable size PK-blender. The blend in the larger bag was passed through a #20 hand screen into the PK-blender. Eighth and ninth separate portions of MCC were utilized to obtain any MCC/ tanaproget remaining residue from larger bag, which residue was passed through a #20 hand screen into the PK-blender. Croscarmellose sodium was passed through a #20 hand screen into the PK-blender. SLS was passed through a #20 hand screen into the PK-blender. Povidone was passed through a #20 hand screen into the PK-blender. All of the materials in the blender were mixed without intensifier bar activation.

A last portion of MCC was passed through a #20 hand screen into the PK-blender and mixed without the intensifier bar activation. Magnesium stearate was passed through a #30 mesh screen and premixed with the blend containing the last portion of MCC, transferred to the PK-blender, and mixed without intensifier bar activation to form the final blend.

The capsules were filled with about 100 mg of the final blend. The capsules were stored in a poly-lined drum at reduced temperatures and in the absence of light and moisture.

TABLE 8

| Ingredients | Amount (mg) | % wt/wt |
|---|---|---|
| Micronized Tanaproget | 0.10 | 0.10 |
| Microcrystalline Cellulose | 90.15 | 90.15 |
| Croscarmellose Sodium | 6.00 | 6.00 |
| Sodium Lauryl Sulfate | 2.0 | 2.0 |
| Povidone | 1.5 | 1.5 |
| Magnesium Stearate | 0.25 | 0.25 |

All documents listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A pharmaceutical composition comprising micronized tanaproget, or a pharmaceutically acceptable salt thereof, microcrystalline cellulose, croscarmellose sodium, anhydrous lactose, and magnesium stearate.

2. The composition according to claim 1, wherein said tanaproget comprises about 0.08% to about 0.4% wt/wt of said composition.

3. The composition according to claim 1 which degrades less than about 4% over a period of greater than 1 month at temperatures at or greater than about 25° C. and a relative humidity at or greater than about 60%.

4. The composition according to claim 1, wherein the particles of said micronized tanaproget are less than about 10 μm.

5. The composition according to claim 1, wherein the particles of said composition are less than about 125 μm.

6. A pharmaceutical composition for oral administration comprising about 0.0875% wt/wt micronized tanaproget, about 56.31% wt/wt microcrystalline cellulose, about 6% wt/wt croscarmellose sodium, about 37.35% wt/wt anhydrous lactose, and about 0.25% wt/wt magnesium stearate.

7. A pharmaceutical composition for oral administration comprising about 0.35% wt/wt micronized tanaproget, about 56.23% wt/wt microcrystalline cellulose, about 6% wt/wt croscarmellose sodium, about 37.17% wt/wt anhydrous lactose, and about 0.25% wt/wt magnesium stearate.

8. A capsule comprising the composition of claim 1.

9. A pharmaceutical kit comprising a daily dosage unit of said capsule of claim 8.

10. The pharmaceutical kit according to claim 9, comprising a single phase of a daily dosage of said composition over a 21, 28, 31, or 31-day cycle.

11. The pharmaceutical kit according to claim 10, further comprising a placebo.

12. The composition according to claim 1, comprising about 0.05 mg to about 1 mg of tanaproget.

13. A tablet comprising the composition of claim 1.

14. A method of contraception, said method comprising administering the composition of claim 1 to a female patient.

15. A method of hormone replacement therapy, said method comprising administering the composition of claim 1 to a patient.

16. A method of treating uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostrate, said method comprising administering the composition of claim 1 to a patient.

* * * * *